United States Patent [19]

Bronstein et al.

[11] Patent Number: 5,032,381

[45] Date of Patent: Jul. 16, 1991

[54] CHEMILUMINESCENCE-BASED STATIC AND FLOW CYTOMETRY

[75] Inventors: Irena Y. Bronstein, Newton; John C. Voyta, Cambridge, both of Mass.

[73] Assignee: Tropix, Inc., Bedford, Mass.

[21] Appl. No.: 286,725

[22] Filed: Dec. 20, 1988

[51] Int. Cl.$^5$ ............... G01N 31/00; G01N 33/48; G01N 33/15; G01N 33/53

[52] U.S. Cl. ............... 424/9; 424/2; 424/3; 424/7.1; 435/6; 435/4; 435/7.21; 435/7.24

[58] Field of Search ............... 424/2, 3, 7.1, 9; 435/7

[56] References Cited

U.S. PATENT DOCUMENTS 4,475,236 10/1984 Hoffman ............... 382/6
4,665,020 5/1987 Saunders ............... 250/458.1

OTHER PUBLICATIONS

Herzenberg, L. A., et al., *Sci. Amer.* 234:108 (1976).
Kaplow, L. S., et al., *J. Histochem. Cytochem.* 25:590 (1977).
"Practical Flow Cytometry", Howard Shapiro, A. R. Liss, Inc., N.Y., 1985, pp. 9–276.
Truneh, A., et al., *Cytometry* 8:562 (1987).
Smith, R. E., et al., *J. Histochem. Cytochem.* 27:1499 (1979).
Dive, C., et al., *Cytometry* 8:552 (1987).
Goolsby, C., et al. *Cytometry* 9:126 (1988).

*Primary Examiner*—Richard L. Raymond
*Attorney, Agent, or Firm*—Cushman, Darby & Cushman

[57] ABSTRACT

Apparati and methods of use for static and flow cytometry of cells and other particulate matter that eliminate the need for a laser or other external energy source to separate and/or detect differences in cells and other particulate matter wherein components of cells and other particulate matter interact with added thermally, chemically, electrochemically, photochemically or enzymatically decomposible chemiluminescent compounds, to produce light energy emissions optically detectable by said apparati.

48 Claims, 4 Drawing Sheets

CHEMILUMINESCENCE-BASED STATIC AND FLOW CYTOMETRY

BACKGROUND OF THE INVENTION

1. Field of the Invention

This invention relates to the addition of a compound or compounds to a cell-containing fluid sample that permits the sorting and identification of cells based on their distinguishing features without using external energy sources. More particularly, this invention relates to a cell analyzing apparatus and methods for using this apparatus for studying a stream of cells suspended in liquid without the need for an external energy or light source to identify cell or particle distinctions, to quantify such cells or particles, and to separate such cells and particles. Additionally, this invention supplies chemiluminescent compounds usable in such an apparatus with such methods that enable rapid, inexpensive differentiation and quantification of naturally occurring cells and subcellular particles. This invention also relates to the use of the aforementioned compounds for the identification of particular cells under static conditions of cytometry.

2. Description of Related Art

Instrumental analysis of cells can be conveniently divided into four stages: (a) cell preparation, (b) "marking" cells, (c) instrument performance, and (d) data analysis (Schema 1).

Several forms of cells exist in the general circulation of mammals. There are red blood cells which are small ovoid cells without nuclei containing large amounts of hemoglobin which serve to deliver oxygen to peripheral cells and remove carbon dioxide. There are leukocytes, which are larger nucleated cells found, on sedimentation, in the "white" or buffy coat above the red cells. There are at least three populations of leukocytes: (1) a lymphocyte population; (2) a monocyte population; and (3) a granulocyte population which includes neutrophils, eosinophils and basophils. Monocytes contain large nuclei with little cytoplasm. Granulocytes are so named because on staining with hemotoxylin and eosin stains, they are shown to contain cytoplasmic granules. Neutrophils contain non-staining granules, eosinophils contain granules which stain with eosin, and basophils contain granules which stain blue after the administration of an acid wash.

"Marking" of cells comprises either exploiting the physical properties or the biochemical properties of cells.

Cells are distinguished by their physical properties using the Coulter principle disclosed by Coulter Electronics, Inc., Hialeah, FL in U.S. Pat. Nos. 2,656,508, 3,259,842 and 3,603,875. Based upon this principle, cell counting and measuring devices typically employ sensing means that respond to induced changes in electrical resistance or some other electronically measurable parameter in order to count and measure each cell and progressively record cell size and content parameters of a sample of cells suspended in an isotonic electrolyte solution. According to the Coulter principle, when a particle of microscopic size (e.g., a blood cell) passes through an electrical field, there will be a momentary change in the electric impedance in the ambit of the field. The electrical change caused by the passage of a particle through an electrical field of small dimension excited by a direct or low frequency current of high energy is closely proportional to the size and volume of the particle. The electrical pulse in such instruments is produced from an external source.

Using this same basic system, differences in cells created by the composition of the cell can also be amplified. For example, Coulter U.S. Pat. No. 3,502,974 discloses that if the applied current is of sufficiently high frequency, the detectable changes that are produced by the passage of particles are a function, not only of size Schema 1
Overall schema for instrumental analysis of cytochemically stained cells.

and volume, but of other physical properties as well, e.g., "opacity" to the electrical field as the result of particle composition. Such qualitative differences can be amplified, detected, then automatically classified.

Identification and separation of normal human leukocytes by volume distribution or other physical characteristics using electrical resistance changes in an applied field, which is the principle of counting and sizing employed by the Coulter Counter instruments, has drawbacks The method is based on the property of all living cells to maintain a certain size and shape. Indeed, each type of cell in the circulating blood has its own characteristic volume ranging from as small as three cubic microns (platelets) to 650 cubic microns for the granulocytes. However, these characteristics are highly variable within the population group with considerable overlap, particularly in diseased states. Advanced Coulter Counters have been designed to make use of such variations in size distribution of platelets, leukocytes, and erythrocytes to detect and monitor pathological states.

Attempts to enhance accuracy have concentrated on alternative means to amplify modest and marginally detectable size differences. Lysing agents have been added to the sheath fluids. Changes in the lysing fluid, which may modify the sizes incrementally, have served to extend the commercial benefits of the basic methodology. These techniques are disclosed in Coulter U.S. Pat. Nos. 4,485,175 and 4,374,644, that disclose the use of particular lysing agents to differentially and gradually modify cell size, and Coulter U.S. Pat. Nos. 4,528,274 and 4,521,518, where the sheath fluid contains charged chemicals that are surface active and thereby enhance charge differences seen between leukocyte populations. Also, see Coulter U.S. Pat. No. 4,555,284 for the use of an osmotic shock agent for a similar purpose.

Devices which make use of combinations of these accuracy enhancing techniques are also known in the art, such as instruments which use a lysing fluid or sheath fluid to modify a physical characteristic such as "electrical opacity" to enhance particle identification, as in Coulter U.S. Pat. No. 3,836,849.

To meet industry needs in this regard, techniques other than ones relying on induced changes in applied electrical fields have been developed to sort and count particular cell populations. But, prior to this invention, no successful method of cell identification or separation using spontaneous light emissions induced by enzymatic cleavage of particular synthetic molecules had been developed.

Until now, the detection by automated instruments of cell differences has required the addition of energy, the scatter, absorption or excitation light reemission of which can be measured by optical or energy sensors. Briefly, as a cell-containing fluid stream passes by an optical or other energy detector, an energy source such as a laser, an electromagnet, or electrical current is directed at the stream. By measuring scattered, absorbed or reemitted energy from the external source, the energy detector or sensor can detect small volume differences or other physical characteristics of the unchanged cell. Additionally, as noted above, the cell can be modified by sheath fluid technology to amplify known physical characteristics. This information is then automatically transmitted to electronically activated deflectors, which can separate the cells by size, or the apparatus can simply count the number of cells within each size category.

Flow cytometers operate on a similar principle. A fluid that contains a known amount of particles per unit volume passes by a sensor. When external energy such as light from a laser, or electromagnetic radiation from an electromagnet, is directed into such a flowing fluid, the particles will scatter, absorb or reemit such energy dependent on characteristics peculiar to such particles. Scattered, absorbed or reemitted energy can be measured by a sensor. The exact amount of such energy received by a sensor per unit time gives a direct indication of the quantity of particles that have passed by in the stream. By knowing the number of such particles per unit volume, the amount of volume per unit time that has passed by can be calculated with an automated instrument—this is, of course, the flow rate Cellular flow cytometers, as in the instant invention, operate by the same principle except that the particles being assayed are cells or subcellular particulate matter, e.g., lysosomes, nuclei, etc.

Sheath fluids used in the standard Coulter technique contain compounds that amplify distinguishing physical features already found in cell populations. Thus, osmotic agents amplify size difference. Paramagnetic agents amplify intrinsic magnetic differences. The sheath fluids used in practicing this invention, however, are radically different from such prior art sheath fluids in that a feature that is not normally automatically detectable, i.e., the presence of a particular species of enzyme or antigen associated with a particular cell population, is made visibly detectable without the need for additional incident energy. In other words, the present invention discloses a technique to make apparent a distinction in the population of whole unseparated cells not normally appreciated by physical instruments.

Generally, prior art devices for detecting cells or distinguishing features of cells required the administration of highly focussed energy, usually electrical, but also electromagnetic radiation, and frequently optically detectable light from a laser or other source. This energy is required because radiation or light detectors or sensors measure scattered, absorbed or reemitted radiation, rather than measuring energy which is spontaneously released or emitted from the cells or particles. Typically, there is no spontaneous emission of radiation from the cells that is usefully counted, sorted, or measured. Any spontaneous energy emission that does occur naturally is either too low in energy level or too infrequently released to be reliably measured by relatively inexpensive instruments. Additionally, induced emissions share these same characteristic difficulties. Thus, added compounds that may produce fluorescence require the administration of external radiation to stimulate optically detectable energy emission. Such an emission is not, therefore, a spontaneous emission within the meaning of the present invention, as fluorescent emissions require the prior or contemporaneous administration of radiation. Additionally, fluorescent radiation is generally of limited temporal duration, which makes it impossible to design a reliable, inexpensive and rapid cell counter based on such emissions. The same principles apply to phosphorescent emissions. Thus, a spontaneous emission that is satisfied by the present invention is measurable by relatively inexpensive instruments, and is of sufficient temporal duration to permit measurement during automatic processing of the fluid containing the cells.

Another means for "marking" individual cells, whether for purposes of static (e.g., microscopic) or flow cytometry, is by cytochemical staining. The principle underlying cytochemical staining is that components of a cell, e.g., a cell surface receptor glycoprotein or an intracellular lysosomal enzyme, can be visualized if one reacts with such component a chemical that becomes colored after reaction (light microscopy) or that fluoresces after reaction by activation by an external light source (fluorescence microscopy). For example, an azo-dye technique for staining monocytes for non-specific intracellular esterase activity has been combined with computer-assisted flow cytophotometry to assess esterase activity in monocytes suspended in a mixed cell population. Kaplow, L.S., et al., *J. Histochem. Cytochem.* 25:590 (1977). Although this was a marked improvement over classical light microscopic techniques in which it was required that the operator's eyes identify cells based upon form and color, colorimetry is noted for its insensitivity, being limited to about $10^{-4}$M concentration of the substance detected.

In another example, low receptor numbers on lymphocytes, fibroblasts and epithelial cells were detected by first reacting such receptors with a fluorochrome such as carboxyfluorescein (delivered to the cell covalently linked to protein A, after treating the cells with anti-receptor antibodies), then subjecting the stained cells to fluorescence-based flow cytometry. Dive et al., *Cytometry* 8:552 (1987). Although fluorescence-based techniques are more sensitive than are colorimetric methods, fluorescence measurements are still limited to about $10^{-5}$ to $10^{-6}$M concentrations of the compound detected due to high backgrounds and reabsorption of the signal by the fluorophore. Thus, the major disadvantages of dye-based optical methods, whether in the static or flow cytometric modes are: (a) lack of sensitivity, and (b) in the case of fluorescence measurements the requirement for an external energy, i.e., light, source.

Therefore, a great need exists for a method for detecting individual cells that is both ultrasensitive and that obviates the need for any external electrical or energy source.

SUMMARY OF THE INVENTION

It has been discovered that individual cells and subcellular particulates may be analyzed, or detected and separated, without the need for an external energy source by reacting endogenous or added components of cells and other particulate matter with added thermally, chemically, electrochemically, photochemically or enzymatically decomposable chemiluminescent compounds to produce optically detectable light energy emissions.

It is an object of the invention to provide methods that use a chemiluminescent chemical compound that, when added to a suspension containing cells derived from an animal or plant source or any other type of subcellular particulate matter, is capable of creating measurable differences in such cells or particles, i.e., the emission of measurable energy, and in particular luminescence or visible light.

It is a further object to provide devices that use these differences to count, sort, or otherwise detect distinguishing features of such cells or particles, in both flow and static cytometry modes, without the use of an external energy source such as a laser or other high energy source.

It is another object of the present invention to enable the construction of flow and static cytometers that are simpler and cheaper than those hitherto available, that can be used, not only in professional laboratories, but also in a physician's offices or other decentralized location. The absence of a laser or other high energy source to stimulate fluorescence, or other photodetection means, permits the dissemination of inexpensive cell sorting, cell counting, and flow cytometer technology.

DETAILED DESCRIPTION OF THE INVENTION

The apparati and methods of this invention make use of known chemiluminescent chemical compounds. These chemiluminescent molecules can first be attached in an art-recognized manner, as described below, to a sample of cells or particles being sorted, counted or otherwise measured, or to cells or particles in a fluid whose rate of flow is being measured in an apparatus embodying the present invention. The thus-attached chemiluminescent molecules will then be cleaved by a suitable activating means also present in, or added to, the cells or particles to decompose such chemiluminescent molecules to yield a moiety in an excited state that emits optically detectable energy.

Alternatively, the chemiluminescent molecules can be added to the cell or particle suspension extraneous to the cells or particles themselves but cleavable by a suitable activating means attached to or otherwise part of the cells or particles.

Any chemiluminescent chemical compound that can be induced to decompose to yield a moiety in an excited state, and particularly chemiluminescent chemical compounds soluble in an aqueous medium, can be used in practicing this invention.

Dioxetanes such as the enzymatically cleavable, water-soluble 1,2-dioxetanes disclosed in copending and commonly assigned Bronstein U.S. patent application Ser. No. 889,823, "Method of Detecting Substances Using Enzymatically-Induced Decomposition of Dioxetanes," filed July 24, 1986; Bronstein et al. U.S. patent application Ser. No. 140,035, "Dioxetanes for Use in Assays," filed Dec. 31, 1987, now abandoned, and Edwards U.S. patent application Ser. No. 140,197, "Synthesis of 1,2-Dioxetanes and Intermediates Therefor," filed Dec. 31, 1987; Bronstein et al., U.S. patent application Ser. No. 213,344, filed June 30, 1988, "Improved Methods of Using Chemiluminescent 1,2-Dioxetanes"; now U.S. Pat. No. 4,931,223, Voyta et al., U.S. patent application Ser. No. 203,263, filed June 1, 1988, "Chemiluminescence Enhancement", and Edwards et al., U.S. patent application Ser. No. 213,672, filed June 30, 1988, "Novel Chemiluminescent Fused Polycyclic Ring-Containing 1,2-Dioxetanes and Assays in Which They Are Used", now U.S. Pat. No. 4,952,707, and their thermally, chemically and electrochemically cleavable analogs form one class of usable chemiluminescent compounds. These 1,2-dioxetanes can be represented by the general formula:

(I)

In this formula T is a stability-providing, unsubstituted or substituted cycloalkyl, aryl, polyaryl or heteroatom group, e.g., an unsubstituted cycloalkyl group having from 6 to 12 ring carbon atoms, inclusive; a substituted cycloalkyl group having from 6 to 12 ring carbon atoms, inclusive, and having one or more substituents which can be an alkyl group having from 1 to 7 carbon atoms, inclusive, or a heteroatom group which can be an alkoxy group having from 1 to 12 carbon atoms, inclusive, such as methoxy or ethoxy, a substituted or unsubstituted aryloxy group, such as phenoxy or carboxyphenoxy, or an alkoxyalkyloxy group, such as methoxyethoxy or polyethyleneoxy, or a cycloalkylidene group bonded to the 3-carbon atom of the dioxetane ring and having from 6 to 12 carbon atoms, inclusive, or a fused polycycloalkylidene group bonded to the 3-carbon of the dioxetane ring and having two or more fused rings, each having from 5 to 12 carbon atoms, inclusive, e.g., an adamant-2-ylidene group.

The symbol X represents hydrogen or an alkyl, aryl, aralkyl, alkaryl, heteroalkyl, heteroaryl, cycloalkyl or cycloheteroalkyl group, e.g., a straight or branched chain alkyl group having from 1 to 7 carbon atoms, inclusive; a straight or branched chain hydroxyalkyl group having from 1 to 7 carbon atoms, inclusive, or an -OR group in which R is a $C_1$-$C_{20}$ unbranched or branched, unsubstituted or substituted, saturated or unsaturated alkyl, cycloalkyl, cycloalkenyl, aryl, aralkyl or aralkenyl group, fused ring cycloalkyl, cycloalkenyl, aryl aralkyl or aralkenyl group, or an N, O or S hetero atom-containing group, or an enzyme-cleavable group containing a bond cleavable by an enzyme to yield an electron-rich moiety bonded to the dioxetane ring. Preferably X is a methoxy group.

The symbol Y represents a light-emitting fluorophore-forming fluorescent chromophore group capable of absorbing energy to form an excited energy state from which it emits optically detectable energy to return to its original energy state.

The symbol Z represents hydrogen (in which case the 1,2-dioxetane can be thermally cleaved via rupture of the oxygen-oxygen bond), a chemically cleavable group such a hydroxyl group, an alkanoyl or aroyl ester group, or an alkyl or aryl silyloxy group, or an enzyme-cleavable group containing a bond cleavable by an enzyme to yield an electron-rich moiety bonded to the fluorophore Y ring, e.g., a bond that, when cleaved, yields an oxygen anion, a sulfur anion or a nitrogen anion, and particularly an amido anion such as a sulfonamido anion.

One or more of the substituents T, X and Z can also include a substituent that enhances the water solubility of the 1,2-dioxetane, such as a carboxylic acid, e.g., acetic acid, a sulfonic acid, e.g., methanesulfonic acid, or a quaternary amino salt, e.g., ammonium bromide. This facilitates thorough mixing of the dioxetane with suspended cells or particles, and, in the case of the former, also permits the maximal penetration of the cells by the dioxetane en route to cleavage by the intracellular triggering means.

Included among the substances whose residues can be present in such 1,2-dioxetanes as fluorescent chromophore Y groups are:
1) anthracene and anthracene derivatives, e.g., 9, 10-diphenylanthracene, 9-methylanthracene, 9-anthracene carboxaldehyde, anthrylalcohols, and 9 phenylanthracene;
2) rhodamine and rhodamine derivatives, e.g., rhodols, tetramethyl rhodamine, tetraethyl rhodamine, diphenyldimethyl rhodamine, diphenyldiethyl rhodamine, and dinaphthyl rhodamine;
3) fluorescein and fluorescein derivatives, e.g., 5-iodoacetamido fluorescein, 6-iodoacetamido fluorescein, and fluorescein-5-maleimide;
4) eosin and eosin derivative, e.g., hydroxy eosins, eosin-5-iodoacetamide, and eosin-5-maleimide;
5) coumarin and coumarin derivatives, e.g., 7-dialkylamino-4-methylcoumarin, 4-bromoethyl-7-methoxycoumarin, and 4-bromomethyl-7-hydroxy coumarin;
6) erythrosin and erythrosin derivatives, e.g. hydroxy erythrosins, erythrosin-5-iodoacetamide and erythrosin-5-maleimide;
7) aciridine and aciridine derivatives, e.g., hydroxy acridines and 9-methyl aciridine;
8) pyrene and pyrene derivatives, e.g., N-(1-pyrene)iodoacetamide, hydroxy pyrenes, 1-pyrene methyl iodoacetate;
9) stilbene and stilbene derivatives, e.g., 6,6'-dibromostilbene and hydroxy stilbene;
10) naphthalene and naphthalene derivatives, e.g., 5-dimethylamino naphthalene-1-sulfonic acid and hydroxy naphthalene;
11) nitrobenzoxadiazoles and nitobenzoadiazole derivatives, e.g., hydroxy nitrobenzoxadiazoles, 4-chloro-7-nitrobenz-2-oxa-1,3-diazole, 2-(7-nitrobenz-2-oxa-1,3-diazol-4yl) methylaminoacetaldehyde, and 6-(7-nitrobenz-2-oxa-1,3-diazol-4-yl-aminohexanoic acid;
12) quinoline and quinoline derivatives, e.g., 6-hydroxyquinoline and 6-aminoquinoline;
13) acridine and acridine derivatives, e.g., N-methylacridine and N-phenylacridine;
14) acidoacridine and acidoacridine derivatives, e.g. 9-methylacidoacridine and hydroxy-9-methylacidoacridine;
15) carbazole and carbazole derivatives, e.g., N-methylcarbazole and hydroxy-N-methylcarbazole;
16) fluorescent cyanines, e.g., DCM (a laser dye) hydroxy cyanines, 1,6-diphenyl-1,3,5-hexatriene, 1-(4-dimethyl aminophenyl)-6-phenylhexatriene, and the corresponding 1,3-butadienes;
17) carbocyanine and carbocyanine derivatives, e.g. phenylcarbocyanine and hydroxycarbocyanines;
18) pyridinium salts, e.g., 4(4-dialkyl diamino styryl) N-methyl pyridinium iodate and hydroxy-substituted pyridinium salts;
19) oxonols; and 20) resorofins and hydroxy resorofins.

When using an enzymatically-cleavable 1,2-dioxetane, cleavage can be accomplished using an enzyme such as an alkaline phosphatase that will cleave a bond in, for example, a Z substituent such as a phosphate ester group to produce a Y anion in a charge transfer state that will, in turn, destabilize the dioxetane and cleave its oxygen-oxygen bond. Cleavage can also be accomplished by using an enzyme such as oxidoreductase enzyme that will cleave the oxygen-oxygen bond directly; see the aforementioned Bronstein and Bronstein et al pending U.S. patent applications.

Besides a phosphate ester group, Z in formula I above can be an enzyme-cleavable alkanoyloxy group, e.g., an acetate ester group, or an oxacarboxylate group, 1-phospho-2,3-diacylglyceride group, 1-thio-D-glucoside group, adenosine triphosphate analog group, adenosine analog group, α-D-galactoside group, β-D-galactoside group, α-D-glucoside group, β-D-glucoside group, α-D-mannoside group, β-D-mannoside group, β-D-fructofuranoside group, β-D-gluosiduronate group, p-toluenesulfonyl-L-arginine ester group or p-toluenesulfonyl-L-arginine amide group.

Preferred enzymatically-cleavable 1,2-dioxetanes for use in practicing this invention are the 3-(2'-adamantyl)-4 methoxy-4-(3''-phosphoryloxy)phenyl-1,2-dioxetane salts represented by the formula:

wherein $M^*$ represents a cation such as alkali metal, e.g., sodium or potassium, ammonium, or a $C_1$–$C_7$ alkyl, aralkyl or aromatic quaternary ammonium cation, $N(R_2)_4^*$ in which each $R_2$ can be alkyl, e.g., methyl or ethyl, aralkyl, e.g., benzyl, or form part of a heterocyclic ring system, e.g., pyridinium, and particularly the disodium salt.

Another class of chemiluminescent compounds usable when practicing this invention includes acridinium esters or the phenanthradinium derivatives in which a phenoxycarbonyl group is present in the 9-position on an N-substituted acridine moiety, e.g., those having the general formula:

wherein $R_3$ is, for example, a $C_1$–$C_{10}$ straight or branched chain alkyl or alkoxy group; an aryl group, preferably one having a single aryl ring, e.g., phenyl; an amino group; a hydroxyl group, a carbonyl-containing group; e.g., an acetyl group, or a carboxylic acid or ester group; $R_4$ can be any of $R_3$, hydrogen, a fused benzo ring, or a group suitable for conjugation to proteins or nucleic acids, e.g., an isothiocyanate group, an N-hydroxysuccinimide ester group, biotin or avidins, and $X_2$ is a counterion that can include, alone or in combination, a halide, sulfate, alkylsulfonate, arylsulfonate, substituted arylsulfonate, perchlorate, alkanoate, arylcarboxylate, heteroarylcarboxylate, phosphate or substituted monoaryloxyphosphate moiety, an anionic oligomer or an anionic homopolymer or copolymer.

These acridinium esters, when attached to cells via antibodies or other ligands, in the presence of a peroxide such as hydrogen peroxide and an alkaline substance, e.g., sodium hydroxide or potassium hydroxide, chemiluminesce from the excited state of the N-substituted acridone formed by cleavage of the phenoxy ester portion of the molecule.

Lucigenin, phosphorylated lucigenin, luciferin, phosphorylated luciferin and the like can also be used as the chemiluminescent molecules when practicing this invention.

Attachment of chemiluminescent chemical compounds to the cells or particles being sorted, counted or otherwise measured, or to the cells or particles in a fluid whose rate of flow is being measured in an apparatus embodying this invention, when this is the desired mode of operation, can be accomplished by art-recognized methods such as: (a) adding the chemiluminescent compound to the extracellular fluid so that it penetrates the cell and reaches the enzyme of interest that decomposes and activates said chemiluminescent compound; (b) covalently attaching the required chemiluminescent compound-cleaving enzyme to an antibody specific for a surface antigen of a cell of interest, mixing this complex with the cells, then adding the chemiluminescent substrate for the enzyme; or (c) sequentially treating the cells of interest with an antibody specific for the cell's surface, with protein A covalently linked with an enzyme, then with the chemiluminescent compound cleavable by said enzyme. Those skilled in the art of cell biology will know of numerous other ways with which to direct the chemiluminescent compounds used in practicing this invention and the related enzyme to particular cell types.

Chemiluminescent compounds that emit light energy when chemically activated can be attached to cells or other particulates by specific antibodies or other suitable ligands, and the compounds reacted with suitable reagents to emit measureable light energy.

In addition, Voyta et al., U.S. Ser. No. 203,263, supra, teach the stabilization, and hence the light intensity, of light-emitting fluorophores produced by the decomposition of chemiluminescent chemical compounds in aqueous media by the addition of certain water-soluble naturally-occurring and synthetic substances, generally macromolecular in nature, for example, water-soluble globular proteins that include hydrophobic regions, such as mammalian serum albumin, or water-soluble polymeric quaternary ammonium salts such as poly[vinylbenzyl(benzyl-dimethyl ammonium chloride)]. Such stabilizers will improve the sensitivity of the static or flow cytometric methods of the invention.

Whether attached to the surface of cells or particles and hence cleavable by a suitable extraneous activating means, or unattached, and hence cleavable by an activating means within the cells or particles, these chemiluminescent chemical compounds, when cleaved, will emit temporally persistent electromagnetic radiation, preferably luminescence of visible light, and thus will be sortable, countable or otherwise measurable using the apparatus of this invention.

Enzyme cleavage, using enzymes coupled to antibodies in a technique well-known in the art based on work by Avrameas [Avrameas, *Int. Rev. Cytol.*, 27:349 (1970)], is a preferred activating means. Antibodies, either polyclonal or monoclonal, can be developed for use as ligands in such binding that are specific for cellular receptors found only on specific cell types. When such covalent antibody-enzyme conjugates are added to the extracellular fluid prior to cytometry, they will bind only to specific cell types. Subsequent addition of the chemiluminescent chemical compound that is cleaved by the enzyme chosen for conjugation will result in the emission of light only from those cells that contain the specific binding sites. Specific cell types can be counted and separated through the use of such antibody-enzyme conjugates and specific chemilmminescent chemical compounds. Examples of specific affinity substances include antibodies, e.g., anti-T4 cell antigen such as $CD_4$, where the substance being detected is the $CD_4$ receptor on T4 lymphocytes; or a probe capable of binding to all or a portion of a nucleic acid, e.g., DNA or RNA, being detected. Bonding between the antibody and the conjugated enzyme is preferably through an amide bond.

In cases where cells are being measured, it is advantageous to preincubate cells with the chemiluminescent substrate so as to allow time for the penetration of the compound into the cells.

Figure 1:
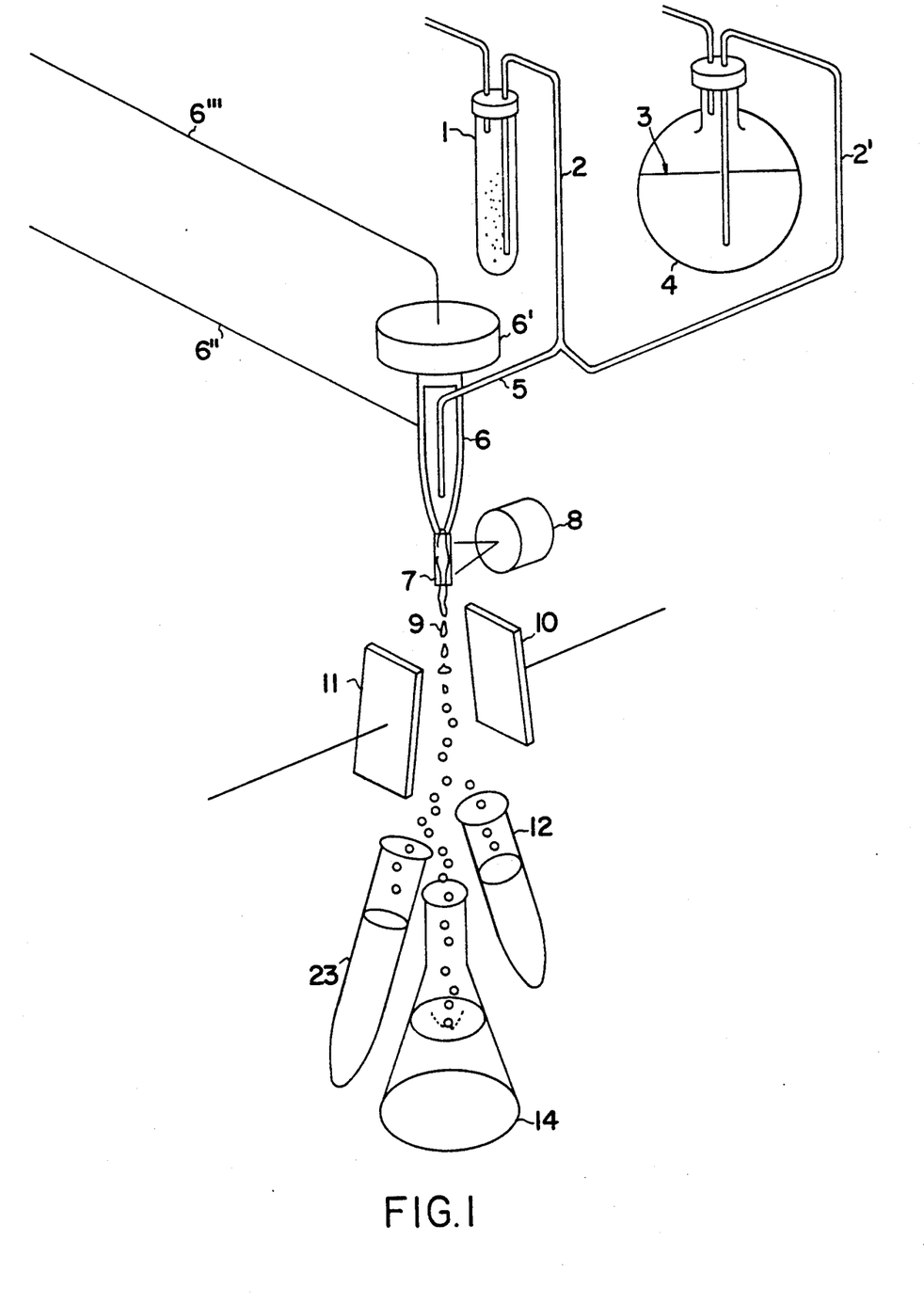
FIG. 1 is a schematic representation of a flow cytometry apparatus constructed in accordance with this invention for use as a cell or particle sorter.

When practicing this invention to sort cells, and with reference to an apparatus as depicted in FIG. 1 being used to sort different types of white cells in samples of human blood, venous blood samples may be drawn from volunteers or patients into evacuated tubes containing an anti-coagulant, e.g., disodium EDTA. The samples may be verified for normalcy by a Coulter Counter before use on the day of drawing. Such data are useful as a screening tool for calling attention to abnormal leukocyte ratios. Abnormal situations identified by this method give information of diagnostic significance.

Appropriate dilutions of cells (e.g., 1:100) may be made in plastic vessels and shaken gently to give homogeneous suspensions. These dilutions can be made with isotonic salt solutions or other suitable fluid.

The cells in suspension are aspirated from a sample tube 1 into internal tubing 2-2' that combines the cells with a sheath fluid 3 contained in an internal beaker 4.

Upon mixing the cells with a chemiluminescent substrate, contained in the internal beaker 4 within a relatively small amount of time enzyme activation of the substrate occurs. Alternatively, reagents are added that activate a chemiluminescent compound. Such activation results in the spontaneous emission of detectable electromagnetic radiation which is temporally persistent. In another alternative method, cells may be preincubated with a chemiluminescent substrate and the substrate activated prior to analysis.

To facilitate the measurement of white cells, and eliminate the red cells, sheath fluids may contain any one of a number of substances, such as lysogenic chemical, well-known in the art of cell counting, to either completely lyse red cells, or partially destabilize the membranes of the white cells as well.

A fluid stream containing the sheath fluid and the cells in suspension, now with adsorbed and/or absorbed chemiluminescent substrate, is directed through the tubing 2-2' and 5 to a nozzle 6 to which a drop-charging signal 6" can be transmitted from a charging source (not shown), that can be used without or with an ultrasonic vibrator $6^1$. The fluid stream passes through a flow cell 7 past a light detector (8) that can be either a photomuliplier tube or a silicon diode-type chemiluminescence detector. The light detector 8 then measures emitted light which arises from the activation of the chemiluminescent chemical compound by the intracellular, cell surface or antibody-bound enzymes. The nozzle 6 can be an ultrasonically vibrated $6^1$ nozzle that causes droplets to be created by a drop-forming signal 6''' from a source (not shown). Such ultrasonic devices are well known in the art. The chemiluminescent chemical compound can be chemically varied in such a fashion that only particular enzymes will result in activation and spontaneous light emission. Such chemical modifications can be made to select enzymes that are particular to the cells being sorted or counted. For example, more than one chemiluminescent 1,2-dioxetane can be used, each compound being configured by means of inclusion of a different light-emitting fluorophore in each of them, to emit light of different wavelengths by decomposing each compound by means of a different enzyme, as described in copending and commonly assigned patent applications, Bronstein et al., U.S. Ser. No. 213,344, filed June 30, 1988, now U.S. Pat. No. 4,931,223, and Edwards et al., U.S. Ser. No. 213,672, also filed June 30, 1988, for multi-channel analyses now U.S. Pat. No. 4,952,707. Or, enzymes that are well-known in the art can be linked to antibodies that have binding sites present only on the particular cells to be sorted or counted.

Finally, droplets 9 break off from the stream leaving the nozzle and pass between two highly charged plates (10 and 11) (−2,000 volts (plate 10)- and +2,000 volts (plate 11), respectively). As a particular droplet containing a specific cell or particle passes the plates 10 and 11, instantaneous changes in the plate charge will deflect the charged droplets 9 in the appropriate direction, where they may be collected in flasks 12, 13, and 14. Droplets 9 may be deflected into the three different flask collectors—left 13, right 12, and center 14, the last of these being for the droplets 9 on which no charge had been placed and which, consequently, fall in an undeflected path, or cells which, though charged, are undeflected by the plates 10 and 11, or into as many collectors as there are cell species being sorted.

Figure 2:
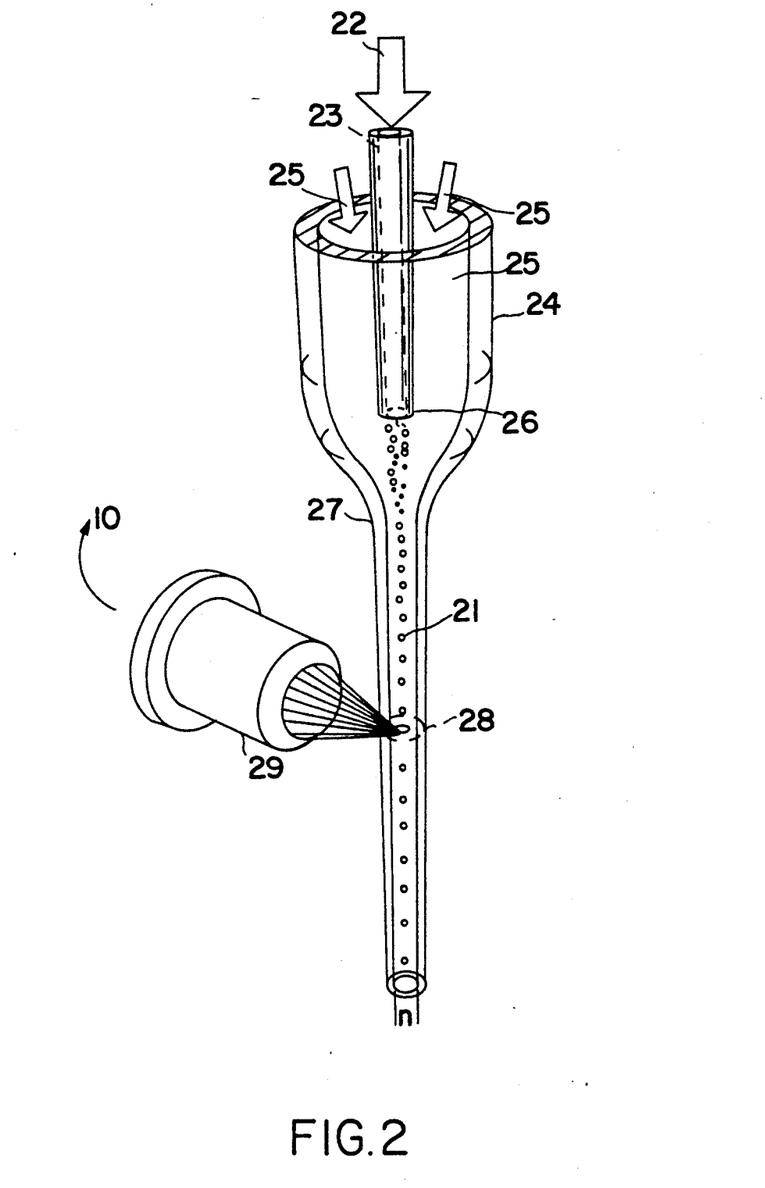
FIG. 2 is a schematic representation of a flow cytometry apparatus embodying the method of the present invention constructed for use in determining distinguishing features of cells or particles.

The chemiluminescence-activated cell sorting system described above and in FIG. 1 can be adapted to determine the distinguishing features of cells and other particulate matter, also without the use of a laser or other external energy source. In a simple flow cytometry mode, the system need not include the deflection plates or collection vessels described in FIG. 1. In the flow cytometry apparatus of FIG. 2, a single file of pretreated cells 21 is produced by introducing the sample or core fluid containing the pretreated cells 22 via a core injection needle 23 through a narrow capillary tube 24 through which a cell-free sheath fluid 25 is flowing from a source (not shown). Flow velocities are adjusted so that flow is laminar, confining the core fluid to the central region of the sheath. Downstream from the injection point 26, the diameter of the tube is reduced, usually by a gradual tapering of the tube 27, to prevent any disturbance of the laminar flow. Although the direction of flow shown in FIG. 2 is downward, the flow cytometer can be arranged so that cells run up, making it easier to remove bubbles from the fluid system. Different arrangements of the flow ca readily be devised according to specific needs by referring to Shapiro, H. M., "Practical Flow Cytometry", Alan R. Liss, Inc., N.Y., 1985. The observation point 28 at which cells are being measured (the intersection of the axes of the sample stream and the detector optical system) can be, as in FIG. 2, inside the capillary, or it can be within cuvettes with a square or rectangular cross section, or through a flat window. Light-energy emitted by the decomposed chemiluminescent substrates used in practicing this invention may be collected by a collecting lens 29, and the signals then transmitted to a luminescence detector (not shown). The detector is typically a photomultiplier tube (PMT); light falling on it creates current. A highly sensitive photodetection technique, single photon counting which also employs a PMT, is particularly suitable for detection of chemiluminescent signals, as there is essentially no background. Multiple observation points with multiple detectors can be used if multiple wavelengths (arising from the decomposition of several chemiluminescent or fluorescent compounds present) are being detected.

In a typical application of a chemiluminescence flow cytometry method and device incorporating this invention, the proportions of helper/inducer and of cytotoxic/suppressor T-lymphocytes in human blood can be determined by using enzyme-conjugated monoclonal antibodies directed against the T4 (Leu-3, OKT4) antigen to identify the first of these cell types and enzyme-conjugated monoclonal antibodies directed against the T8 (Leu-2, OKT8) antigen to identify the second. Lanier, L. L. et al., *J. Immunol.* 132:151 (1984). One of the enzymes can be alkaline phosphatase and the substrate can then be a chemiluminescent 1,2-dioxetane that is decomposable by a phosphatase, e.g., AMPPD (see supra). The other enzyme can be different, e.g., a galactosidase, and the substrate can then be a chemiluminescent 1,2-dioxetane that is cleavable by the galactosidase, e.g., 3-(2'-adamantyl)-4-methoxy-4-(3''-D-galactopyranosidyl)phenyl-1,2-dioxetane. In this mode, multichannel analyses is utilized (see supra).

In another application, blood cells rich in intracellular alkaline phosphatase, e.g., neutrophil granulocytes, can be identified and quantified by incorporating AMPPD into the extracellular fluid (reference numeral 1 in FIG. 1; reference numeral 2 in FIG. 2), then measuring the luminescence produced by the decomposition of substrate AMPPD by the intracellular enzyme.

In any application, the pH of the sheath fluid should be optimal for enzyme activity (e.g., pH 9.5 for alkaline phosphatase and pH 6.5 for β-galactosidase). However, as chemiluminescence intensity from, e.g., decomposed 1,2-dioxetanes, is maximal at pH 9.5 or greater, a device embodying the invention should be modifiable so as to provide for the addition of base to the fluid stream at a point just before the point of observation for the optical detector(s). Thus, enzyme-catalyzed decomposition of, e.g., 1,2-dioxetane, can be carried out at the optimum pH for enzyme activity, and chemiluminescence can be detected at its optimum (i.e., alkaline) pH.

Several illustrations of cytostaining coupled with static or flow cytometry will demonstrate the wide scope of this invention. Cells infected with Herpes Simplex Virus-2 are treated with a rabbit or goat antibody raised against the virus, the cells are then exposed to an activating hydrolytic enzyme covalently attached to either goat anti-rabbit serum or rabbit anti-goat serum as the second antibody, a suitable enzyme-cleavable chemiluminescent compound is added, and static and/or flow cytometric analyses of the light emitting cells is then performed by the measurement of light intensity; the difference between infected and non-infected cells will be readily detectable and quantifiable.

Monocytes containing non-specific esterase activity are detectable by flow cytoenzymology, wherein the cells are stained with a chemiluminescent esterase substrate, light is emitted as the substrate is decomposed by the cellular esterase, cells are pumped through the flow cell and sampled continuously and light intensity is detected and quantified by optical means. See Dive et al., supra.

Where static (e.g., slides) cytometry is employed following elicitation of chemiluminescence from cells, the light energy can be imaged in a black box with instant film, e.g., Polaroid's Type 612 film, or the light may be viewed by a camera attached to a microscope, or the light may be visualized by a charge coupled device camera used in conjunction with the microscope.

In order that those skilled in the art can more fully understand this invention, the following examples are set forth. These examples are given solely for illustration, and should not be considered as expressing limitations unless so set forth in the appended claims.

EXAMPLE 1

Neutrophil Imaging on Film

A sample of blood was collected in the presence of the anticoagulant, EDTA. The cells were allowed to settle by gravity for 3 hours. The buffy coat (white blood cells) was removed from above the red blood cells, then isolated by centrifugation. The cells were washed twice with phosphate buffered saline (PBS), then fixed in 10% formalin in PBS at 0° C. for 30 minutes. The fixed cells were then washed twice with PBS, and twice with substrate buffer (50 mM $Na_2CO_3$-1 mM $MgCl_2$, pH 9.5).

Aliquots of cells were then incubated in the following solutions for 30 minutes:
1. 50mM $Na_2CO_3$ buffer, pH 9.5, containing 1 mM $MgCl_2$.
2. Solution 1 plus 1.6 mM AMPPD.
3. Solution 2 plus 10 μg/ml sodium fluorescein.
4. Solution 2 plus 1 mg/ml BDMQ (a chemiluminescence enhancer), 10 μg/ml sodium fluorescein.

Figure 3:
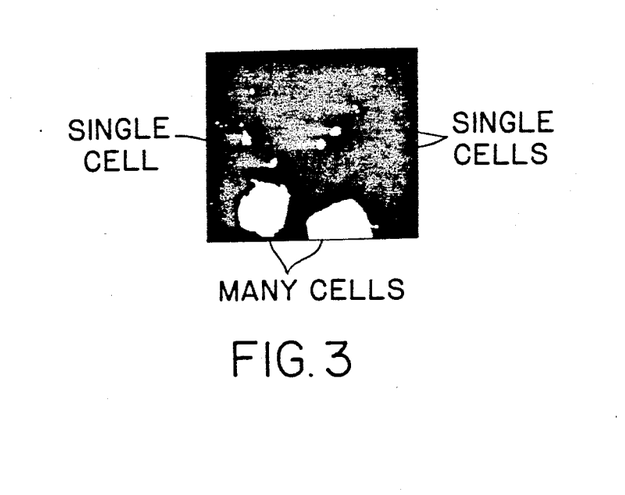
FIG. 3 demonstrates neutrophil detection by the chemiluminescence-based, static cytometric method performed in accordance with the invention.

Aliquots of the cell suspension (Solution 4) were placed on a glass fiber membrane (0.5 $cm^2$) and the membrane placed between two pieces of Mylar ® film into a camera luminometer. The light resulting from one minute exposures was imaged on Polaroid Type 612 film. The images of single neutrophils and colonies of cells on instant film are shown in FIG. 3. Small punctuate areas were observed which corresponded to single neutrophils.

As neutrophils are rich in the alkaline phosphatase that catalyzes decomposition of AMPPD, this method provides a qualitative or semi-quantitative (by applying a densitometer to the positive of the film) assay for this cell type.

EXAMPLE 2
FLOW CYTOMETRY

Cell suspensions from Example 1 were analyzed in a Becton Dickinson Fluorescence Activated Cell Sorter Analyzer. For this experiment, the fluorescence excitation lamp was turned off, and the light detector was used to detect the chemiluminescence signal resulting from the decomposition of AMPPD by neutrophilic alkaline phosphatase.

A sheath fluid of 50 mM $Na_2CO_3$ buffer, pH 9.5, containing 1 mM $MgCl_2$ was used. Data from 10,000 to 20,000 cells of the correct size for neutrophils was then analyzed. The data is summarized in Table 1.

TABLE 1

Detection of Neutrophils by Flow Analysis with AMPPD

| Condition | Average Luminescent Intensity |
|---|---|
| Cells alone | 68.0 |
| Cells and AMPPD | 68.7 |
| Cells and AMPPD and fluorescein | 69.3 |
| Cells and AMPPD and fluorescein and BDMQ | 69.9 |

Slight increases in chemiluminescent signal above background endogenous chemiluminescence were observed by adding AMPPD. The best results were obtained by the addition to neutrophils of AMPPD, using BDMQ and fluorescein to enhance the signal. The signal from the decomposition of AMPPD can be enhanced by using a detector specifically adapted to the wavelength of the light emitted by AMPPD, unlike that provided in the standard Becton Dickinson analyzer.

EXAMPLE 3
IN-SITU HYBRIDIZATION

HSVI infected HEP2 cells were fixed and mounted onto glass microscope slides. The slides were incubated in 0.2N HCl for 2 minutes, rinsed with water, and immersed in 70% ethanol. The slides were then incubated in hybridization buffer (0.5% BSA, 0.5% polyvinylpyrrolidone, 1.0% sodium dodecyl sulphate in 0.075 M NaCl, 0.075M sodium citrate, pH 7.0) at 70° C. for 15 minutes. The slides were subsequently rinsed with 0.3N NaOH and with phosphate buffered saline. The slides were then incubated with an alkaline phosphatase-labeled DNA probe specific for HSVI in the hybridization buffer at 60° C. for 20 minutes. The slides were then washed twice at 50° C. with citrate buffered saline for 5 minutes and once with 0.05M sodium carbonate, 1 mM $MgCl_2$, 0.1% BSA, pH 9.5. Next, 1.6 mM AMPPD (in the previous buffer) was added to the slides and incubated for 5 minutes.

INSTANT FILM IMAGING OF IN-SITU HYBRIDIZATION CELLS

Figure 4:
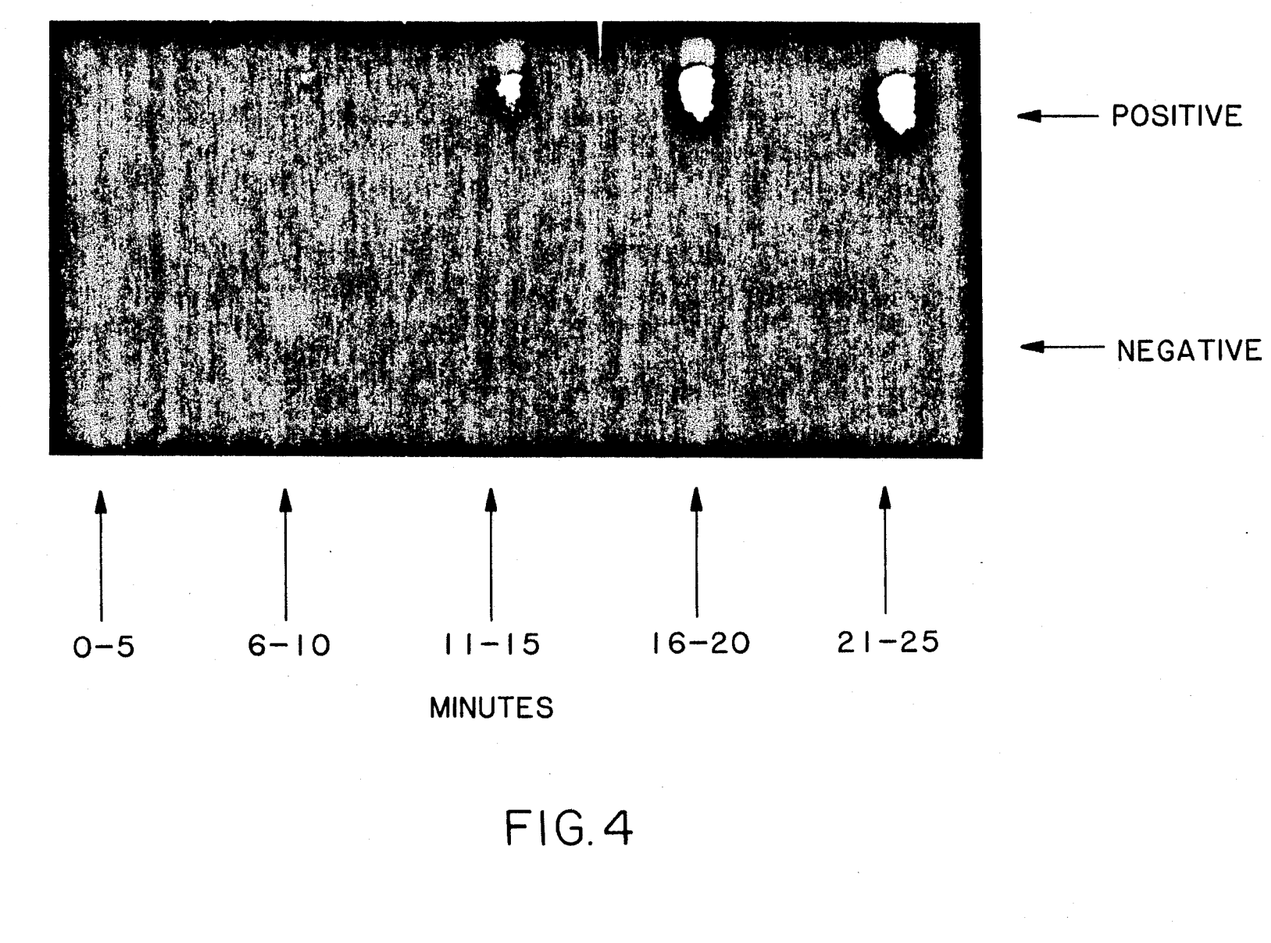
FIG. 4 demonstrates in situ hybridization of Herpes Simples I Virus-infected HEP2 cells, hybridization with an alkaline phosphatase-labeled DNA probe, and detection by the AMPPD chemiluminescence cytometry method of the invention.

The slides were wrapped in plastic and transferred to a black box. Polaroid Type 612 film was then exposed for 5 minute intervals. The results of this exposure are shown in FIG. 4. Very clear differentiation between infected (Positive) and noninfected cells (Negative) was observed.

CHARGE COUPLED DEVICE (CCD) IMAGING OF IN-SITU HYBRIDIZED CELLS

Figure 5:
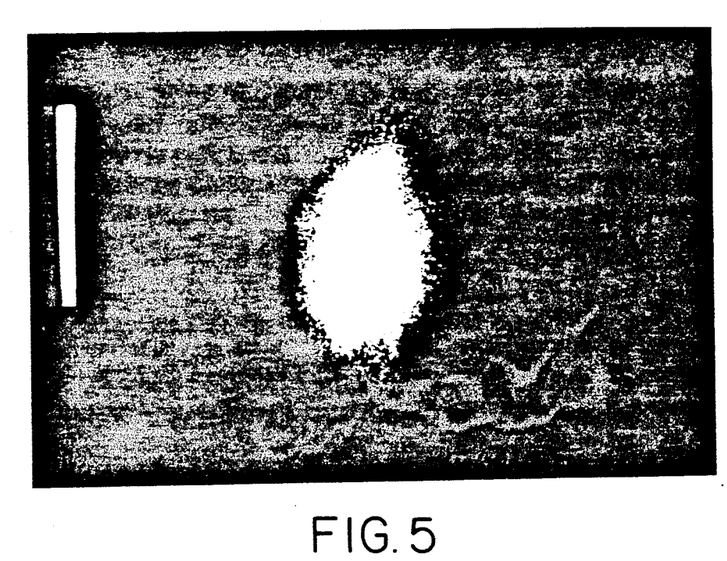
FIG. 5 shows a CCD camera image of HSVI-infected HEP2 cells detected by the DNA probe-chemiluminescence static cytometry method of the invention.

A Photometrics Series 200 CCD imaging camera was fitted with a 50 mm f1.2 Nikon lens and positioned approximately 18 inches from the surface. A hybridized slide treated with AMPPD substrate, was wrapped in plastic and then placed on the surface directly under the CCD camera. A five minute accumulation of light was made on the CCD camera prior to reading. A picture of the image obtained is shown in FIG. 5. No signal was observed from non-infected cells.

We claim:

1. A flow cytometry method for determining the distinguishing features of cells and other particulate matter without the use of a laser or other external source of light energy, comprising the steps of:
   a. producing a suspension medium comprising (1) a sheath fluid in which cells or other particulate matter are suspended, (2) a chemiluminescent chemical compound decomposable to emit measurable light energy in response to the presence of said cells or other particulate matter being determined, and (3) an activating means to cause said chemiluminescent chemical compound to decompose;
   b. passing said suspension medium through the flow cytometer apparatus of FIG. 2; and
   c. detecting the light energy emitted by said decomposed chemiluminescent chemical compound by a light energy detector.

2. The method of claim 1 wherein said chemiluminescent chemical compound comprises a thermally, chemically, electrochemically, photochemically, or enzymatically cleavable 1,2-dioxetane, acridinium ester, lucigenin or luciferin.

3. The method of claim 2 wherein said chemiluminescent compound comprises a water-soluble 1,2-dioxetane.

4. The method of claim 3 wherein said 1,2-dioxetane is enzymatically cleavable.

5. The method of claim 4 wherein said 1,2-dioxetane comprises a 3-(2'-adamantyl)-4-methoxy-4-(3''-phophoryloxy)phenyl-1,2-dioxetane salt.

6. The method of claim 4 wherein said 1,2-dioxetane comprises a 3-(2'-adamantyl)-4-methoxy-4-(3''-O-galactopyranoside)phenyl-1,2-dioxetane.

7. The method of claim 4 wherein said 1,2-dioxetane is 3-(2'-adamantyl)-4-methoxy-4-(3''-acetoxy) phenyl-1,2-dioxetane.

8. The method of claim 1 wherein said activating means comprises an enzyme contained on or within said cell or other particulate matter.

9. The method of claim 1 wherein said activating means comprises one or more enzyme-ligand conjugates wherein said ligand binds to one or more components of said cell or other particulate matter.

10. The method of either claim 8 or claim 9 wherein said enzyme is selected from among a group consisting of a phosphatase, a galactopyranosidase and an esterase.

11. The method of claim 9 wherein said ligand comprises an antibody directed against a component of said cell or other particulate matter.

12. The method of claim 1 wherein said light energy detector comprises a photomultiplier tube.

13. The method of claim 1 further comprising a light energy collecting lens interposed between said light energy source and said light energy detector.

14. A static cytometry method for determining the distinguishing features of cells and other particulate matter without the use of a laser or other external energy source, comprising the steps of:
   a. preparing a suspension medium comprising (1) a fluid in which said cells and other particulate matter are suspended, (2) a chemiluminescent chemical compound decomposible to emit measurable energy in response to the presence of said cells and other particulate matter whose distinguishing features are being determined, and (3) an activating means to cause said chemiluminescent chemical compound to decompose;
   b. viewing said suspension medium with a viewing means operably linked to a light energy detector; and,
   c. detecting said light energy.

15. The method of claim 14 wherein said chemiluminescent chemical compound is a thermally, chemically, electrochemically, photochemically or enzymatically cleavable 1,2-dioxetane, acridinium ester, lucigenin or luciferin.

16. The method of claim 15 wherein said chemiluminescent compound comprises a water-soluble 1,2-dioxetane.

17. The method of claim 16 wherein said 1,2-dioxetane is enzymatically cleavable.

18. The method of claim 17 wherein said cleavable 1,2-dioxetane is a 3-(2'-adamantyl)-4-methoxy-4-(3''-phosphoryloxy)phenyl-1,2-dioxetane salt.

19. The method of claim 17 wherein said cleavable 1,2-dioxetane is a 3-(2'adamantyl)-4-methoxy-4-(3''-O-galactopyranoside)phenyl-1,2-dioxetane.

20. The method of claim 17 wherein said cleavable 1,2-dioxetane is 3-(2'-adamantyl)-4-methoxy-4-(3''-acetoxy)phenyl-1,2dioxetane.

21. The method of claim 14 wherein said measurable energy is optically detectable energy.

22. The method of claim 14 wherein said activating means comprises an enzyme contained on or within said cell or other particulate matter.

23. The method of claim 14 wherein said activating means comprises one or more enzyme-ligand conjugates wherein said ligand binds to one or more components of said cell or other particulate matter.

24. The method of either claim 22 or claim 23 wherein said enzyme is selected from among a group consisting of a phosphatase, a galactopyranosidase and an esterase.

25. The method of claim 23 wherein said ligand comprises an antibody directed against a component of said cell or other particulate matter.

26. The method of claim 14, wherein said viewing means is a microscope and said light energy detector is contained within a camera.

27. The method of claim 26, wherein said light energy detector is photographic film, silicon intensified target, intensified silicon intensified target, charge coupled device or intensified charge coupled device.

28. The method of claim 14, wherein said viewing means is a camera and said light energy detector is photographic film, silicon intensified target, intensified silicon intensified target, charge coupled device or intensified charge coupled device.

29. The method of claim 14, further comprising affixing said cells or other particulate matter to a solid surface prior to said viewing and detecting light energy.

30. The method of claim 29, wherein said solid surface comprises glass, fiberglass or a polymeric membrane.

31. The method of claim 30, wherein said viewing means is a microscope with operably attached camera.

32. The method of claim 31, wherein said camera uses photographic film, silicon intensified target, intensified silicon intensified target, charge coupled device or intensified charge coupled device as said light energy detection component.

33. The method of claim 29, wherein said viewing means is a camera and said light energy detector is photographic film, silicon intensified target, intensified silicon intensified target, charge coupled device or intensified charge coupled device.

34. A static cytometry method for determining the distinguishing features of cells and other particulate matter without the use of a laser or other external energy source, comprising the steps of:
   (a) preparing a suspension medium comprising (1) a fluid in which said cells or other particulate matter are suspended and (2) a chemiluminescent chemical compound decomposable to emit measurable energy in response to the presence of said cells or particulate matter whose distinguishing features are being determined;
   (b) affixing said cells or other particulate matter to a solid surface; and
   (c) contacting said solid surface with a light energy detector.

35. A method of claim 34, wherein said chemiluminescent chemical compound is an enzymatically cleavable 1,2-dioxetane.

36. A method of claim 35, wherein said 1,2-dioxetane is a 3-(2'-adamantyl)-4-methoxy-4-(3''-phosphoryloxy)phenyl-1,2-dioxetane salt.

37. A method of claim 35, wherein said 1,2-dioxetane is a 3-(2'adamantyl)-4-methoxy-4-(3''-O-galactopyranoside) phenyl-1,2-dioxetane.

38. A method of claim 35, wherein said 1,2-dioxetane is a 3-(2'-adamantyl)-4-methoxy-4-(3''-acetoxy) phenyl-1,2-dioxetane.

39. A method of claim 34, wherein said solid surface is glass, fiberglass or a polymeric membrane.

40. A method of claim 34, wherein, said light energy detector is photographic film, silicon intensified target, intensified silicon intensified target, charge coupled device or intensified charge coupled device.

41. A method of claim 34 further comprising addition to said suspension medium of one or more chemiluminescence enhancer compounds.

42. A method of claim 41, further comprising adding to said suspension medium an emission wavelength shifting compound.

43. A static cytometry method for determining the distinguishing features of cells and other particulate matter without the use of laser or other external energy source, comprising the steps of:
   (a) preparing a suspension medium comprising a fluid in which said cells or other particulate matter are suspended;
   (b) affixing said cells or other particulate matter to a solid surface;
   (c) contacting nucleic acids or fragments thereof present in said cells or other particulate matter with a complementary nucleic acid probe to which is covalently bound by an activating means capable of decomposing a chemiluminescent chemical compound to emit light energy;

(d) contacting said bound activating means with said chemiluminescent chemical compound; and (e) detecting said light energy with a light detecting means.

44. A method of claim 43, wherein said chemiluminescent chemical compound is an enzymatically cleavable 1,2-dioxetane.

45. A method of claim 43, wherein said chemiluminescent is a 3-(2'-adamantyl)-4-methoxy-4-(3"'-phosphoryloxy) phenyl-1,2-dioxetane salt.

46. A method of claim 43, wherein said chemiluminescent is a 3-(2'-adamantyl)-4-methoxy-4-(3"O-galactopyranoside) phenyl-1,2-dioxetane.

47. A method of claim 43, wherein said activating means comprises an enzyme selected from among a group consisting of a phosphate, a galactopyranosidase and an esterase.

48. A method of claim 43, wherein said light detecting means is photographic film, silicon intensified target, intensified silicon intensified target, charge coupled device or an intensified charge coupled device.

* * * * *